US008435971B2

(12) United States Patent
Cuevas Sánchez et al.

(10) Patent No.: US 8,435,971 B2
(45) Date of Patent: May 7, 2013

(54) USE OF 2,5-DIHYDROXYBENZENESULFONIC ACID IN THE MANUFACTURING OF MEDICINES, APPLICABLE TO THE TREATMENT OF ANGIODEPENDENT DISEASES

(75) Inventors: Pedro Cuevas Sánchez, Madrid (ES); Antonio Romero Garrido, Madrid (ES); Guillermo Gimenez Gallego, Madrid (ES); Serafin Valverde Lopez, Madrid (ES); Rosa Maria Lozano Puerto, Madrid (ES)

(73) Assignee: AmDerma Pharmaceuticals, LLC, Bridgewater, NJ (US)

( * ) Notice: Subject to any disclaimer, the term of this patent is extended or adjusted under 35 U.S.C. 154(b) by 0 days.

(21) Appl. No.: 13/169,781

(22) Filed: Jun. 27, 2011

(65) Prior Publication Data

US 2012/0142780 A1 Jun. 7, 2012

Related U.S. Application Data

(63) Continuation of application No. 10/588,166, filed as application No. PCT/ES2005/070017 on Feb. 16, 2005.

(51) Int. Cl.
*A61K 31/185* (2006.01)
*A61K 31/56* (2006.01)
*A01N 37/00* (2006.01)
*A01N 45/00* (2006.01)

(52) U.S. Cl.
USPC ............................ 514/171; 514/553; 514/576

(58) Field of Classification Search ................... 514/171, 514/576, 553
See application file for complete search history.

(56) References Cited

U.S. PATENT DOCUMENTS

| | | | |
|---|---|---|---|
| 3,954,767 A | 5/1976 | Esteve-Subirana | |
| 4,115,648 A | 9/1978 | Esteve-Subirana | |
| 4,837,378 A | 6/1989 | Borgman | |
| 4,970,202 A | 11/1990 | Trigger | |
| 5,374,772 A | 12/1994 | Carson et al. | |
| 5,519,018 A | 5/1996 | Matusch et al. | |
| 5,656,286 A | 8/1997 | Miranda et al. | |
| 5,698,595 A | 12/1997 | Boelle et al. | |
| 6,281,203 B1 | 8/2001 | Touzan et al. | |
| 6,664,406 B1 | 12/2003 | Coupland et al. | |
| 6,787,573 B2 | 9/2004 | Nottet | |
| 7,968,531 B2 * | 6/2011 | Cuevas Sanchez et al. | .. 514/171 |
| 2002/0143052 A1 | 10/2002 | Lan-Hargest et al. | |
| 2003/0216418 A1 | 11/2003 | Stogniew et al. | |
| 2004/0167222 A1 | 8/2004 | Brooks et al. | |
| 2005/0175559 A1 | 8/2005 | DiNardo et al. | |
| 2006/0258730 A1 | 11/2006 | Allegretti et al. | |
| 2007/0032471 A1 | 2/2007 | Torrens Jover et al. | |
| 2007/0149618 A1 | 6/2007 | Cuevas Sanchez et al. | |
| 2008/0113947 A1 | 5/2008 | Cuevas Sanchez et al. | |
| 2008/0113948 A1 | 5/2008 | Cuevas Sanchez et al. | |
| 2008/0114060 A1 | 5/2008 | Cuevas Sanchez et al. | |
| 2008/0114063 A1 | 5/2008 | Sanchez et al. | |
| 2008/0114075 A1 | 5/2008 | Cuevas Sanchez et al. | |
| 2008/0125485 A1 | 5/2008 | Cuevas Sanchez et al. | |
| 2008/0125486 A1 | 5/2008 | Sanchez et al. | |
| 2009/0111779 A1 | 4/2009 | Cuevas Sanchez et al. | |

FOREIGN PATENT DOCUMENTS

| | | |
|---|---|---|
| EP | 0204987 | 5/1986 |
| EP | 1719509 | 11/2006 |
| JP | 8283152 | 10/1996 |
| WO | WO-96/17589 | 6/1996 |
| WO | WO-96/25159 | 8/1996 |
| WO | WO-2005/013962 | 2/2005 |
| WO | WO-2005/023305 | 3/2005 |
| WO | WO-2005/077352 | 8/2005 |
| WO | WO-2006/029484 | 3/2006 |
| WO | WO-2006/069806 | 7/2006 |

OTHER PUBLICATIONS

"Actinic Keratosis and Other Precancers", http//www.skincancer.org 2008, 3 pgs.
"Causes of Barrett's Esophagus", http://digestive-system.emedtv.com/barrett's-esophagus/causes-of-barrett's-esophagus.html Nov. 2006, 3 pgs.
"Crohn's Disease", http://cholitis.emedtv.com/crohn'sdisease/crohn's-disease-causes.html 2008, 3 pgs.
"Definition of Rosacea", American Heritage Medical Dictionary, www.freedictionary.com 2007, 6 pgs.
"Psoriasis—Basics Facts—What Is Psoriasis", http://www.psoriasisguide.com/usus_basics/what_is_psoriasis.html 2 pgs., 2005.
"Remington's Pharmaceutical Sciences", 1980, 7 pgs.
"What is Rosacea?". http://www.rosacea.net/, 2005, 1 pg.
Adank, Christian et al., "Calcium Dobesilate in Diabetic Retinopathy", *Ophthalmologica*, Basel 190 1985, 102-111.
Angulo, Javier et al., "Calcium dobesilate potentiates endothelium-derived hyperpolarizing factor-mediated relaxation of human penile resistance arteries", *British Journal of Pharmacology 000* 2003, 1-9.
Anwar, Jamshaid et al., "The Development of Actinic Keratosis into Invesive Squamous Cell Cardinoma: Evidence and Evolving Classification Schemes", *Clinics in Dermatology 22* 2004, 189-196.

(Continued)

*Primary Examiner* — Anna Pagonakis
(74) *Attorney, Agent, or Firm* — Servilla Whitney LLC; Kenneth M. Zeidner (57) ABSTRACT

The invention relates to the use of 2,5-dihydroxybenzenesulfonic acid in the production of medicaments for the treatment of angiodependent diseases. More specifically, the invention relates to the use of the aforesaid compound and, in particular, the calcium and potassium salts thereof, for the treatment of two angiodependent diseases, which present a reduction in the apoptosis, namely cancer and psoriasis. The invention also discloses the antiproliferative, antimigratory, antiangiogenic and proapoptotic capacity of said family of compounds in non-quiescent cells. In addition, the invention details the potentiating effect of said compounds on known cytostatic medicines in the treatment of tumours and, specifically, on gliomas. The invention further relates to the therapeutic efficacy of said compounds, based on the combined antiproliferative, antiangiogenic and proapaptotic capacities thereof, in the treatment of chronic psoriatic plaques.

16 Claims, 9 Drawing Sheets

OTHER PUBLICATIONS

Arhanic, V. et al., "Attempts at Treating Bureosis with Angioprotective Agents", *Annals of the Dr. M. Stojanovic Hospital*, vol. 15:120 1976, 9 pgs.

Benakis, A. et al., "Localisation, distribution, eliination et metabolisme du dihydroxy-2,5, benzene sulfonate de Ca (Dobesilate de Ca) marque par le S35 chez la souris, le rat et le lapin", *Congres International de Therapeutique* 1974, 16 pgs.

Benarroch, Isaac S. et al., "Treatment of Blook Hyperviscosity with Calcium Dobesilate in Patients with Diabetic Retinopathy", *Ophthalmic Res. 17* 1985, 131-138.

Berthet, P. et al., "Calcium Dobesilate: Pharmacological Profile Related to its Use in Diabetic Retinopathy", *IJCP.*, vol. 53, No. 8 Dec. 1999, 631-636.

Bhushan, M. et al., "Recent advances in cutaneous angiogenesis", *British Journal of Dermatology 147* 2002, 418-425.

Brannon, MD, Heather, "Atopic Dermatitis Treatment", http://dermatology.about.com/cs/eczemadermatitis/a/stopictx.htm Dec. 23, 2005, 2 pgs.

Brunet, J. et al., "In vitro antioxidant properties of calcium dobesilate", *Fundam Clin Pharmacol 12* 1998, 205-212.

Catalogo de especialidades farmaceuticas 1991, *Consejo General De Colegios Oficiales De Farmaceuticos* 1991, 4 pgs.

Cuevas, P. et al., "Therapeutic Response of Rosacea to Dobesilate", *Eur. J. Med. Res.*, vol. 10 2005, pp. 454-456.

Cuevas, P. et al., "Treatment of basal cell carcinoma with dobesilate", *Am Acad Dermatol* 2005, 526-527.

Cuevas, P., et al., "Topical Treatment of Actinic Keratoses with Potassium Dobesilate 5% Cream. A Preliminary Open-Label Study", *Eur J. Med Res 16*, 2011, 67-70.

Cuevas, Pedro et al., "Dobesilate in the Treatment of Plaque Psoriasis", *Eur J Med Res 10* 2005, 373-376.

Divers, A.K. et al., "Keratoacanthoma centrifugum marginatum: a diagnostic and therapeutic challenge", *Curtis*, vol. 73, No. 4 2004, 257-262.

Dormond, Olivier et al., "Inhibitor of tumor angiogenesis by non-steroidal anti-inflammatory drugs: emerging mechanisms and therapeutic perspectives", *Drug Resistance Updates 4* 2002, 314-321.

Dorwald, F. Z., "Side Reactions in Organic Synthesis. A Guide to Sucessful Synthesis Design", *Wiley-VCH Verlag GmbH & Co.* 2005, 4 pgs.

English translation of Acnisdin and Acnisdin Retinoico entries in Catalogo de especialidades farmaceuticas, *Consejo General de Colegios Oficiales De Farmaceuticos* 1991, 2 pgs.

Final Office Action in U.S. Appl. No. 12/257,854, dated Mar. 1, 2012, 9 pgs.

Gambichler, T. et al., "Cytokine mRNA expression in basal cell carcinoma", *Arch Dermatol Res 298* 2006, 139-141.

Glioma Brain Tumors, http://www.sfn.org/index.aspx?pagename=brainbriefings_gliomabraintumors 2008, 2 pgs.

Goldman, Lee et al., "Principles of Cancer Therapy", *Cecil Textbook of Medicine*, vol. 1, W.B. Saunders Company 2000, 1060-1074.

Graber, R. et al., "Calcium Dobesilate protects human peripheral blood mononuclear cells from oxidation and apoptosis", *Apoptosis 3* 1998, 41-49.

Hodge, David R. et al., "The role of IL-6 and STAT3 in inflammation and cancer", *European Journal of Cancer 41* 2005, 2502-2512.

Hornick, Jason L. et al., "A New Chemically Modified Chimeric TNT-3 Monoclonal Antibody Directed Against DNA for the Radioimmunotherapy of Solid Tumors", *Cancer Biotherapy & Radiopharmaceuticals*, vol. 13, No. 4 1998, 255-268.

International Search Report of PCT/EP/2007/058440, mailed on Feb. 22, 2008, 5 pages.

International Search Report of PCT/EP2007/058438, mailed on Nov. 27, 2007, 4 pages.

International Search Report of PCT/EP2007/058439, mailed on Nov. 28, 2007, 4 pages.

International Search Report of PCT/EP2007/058440, mailed on Feb. 22, 2008, 5 pages.

International Search Report of PCT/EP2007/058441, mailed on Nov. 14, 2007, 4 pages.

International Search Report of PCT/EP2007/058443, mailed on Nov. 9, 2007, 3 pages.

International Search Report of PCT/EP2007/058444, mailed on Nov. 28, 2007, 4 pages.

International Search Report of PCT/EP2007/058445, mailed on Nov. 26, 2007, 4 pages.

International Search Report of PCT/EP2007/058446, mailed on Nov. 30, 2007, 4 pages.

International Search Report of PCT/EP2007/058447, mailed on Dec. 3, 2007, 4 pages.

International Search Report of PCT/EP2007/058451, mailed on Nov. 30, 2007, 4 pages.

International Search Report of PCT/EP2007/058453, mailed on Jul. 15, 2008, 6 pages.

International Search Report of PCT/EP2007/058454, mailed on Feb. 19, 2008, 4 pages.

International Search Report of PCT/EP2007/058456, mailed on Dec. 6, 2007, 7 pages.

International Search Report of PCT/ES2005/070017, mailed on Jun. 22, 2005, 2 pages.

Jee, S. H. et al., "The Phosphotidyl Inositol 3-Kinase/Akt Signal Pathway is Involved in Interleukin-6-mediated Mcl-1 Upregulation and Anti-apoptosis Activity in Vasal Cell Carcinoma Cells", *The Journal of Investigative Dermatology*, vol. 119, No. 5 2002, 1121-1127.

Jee, Shiou-Hwa et al., "Interleukin-6 Induced Basic Fibroblast Growth Factor-Dependent Angiogenesis in Basal Cell Carcinoma Cell Line via JAK/STAT3 and PI3-Kinase/Akt Pathways", *J Invest Dermatology 123* 2004, 1169-1175.

Jee, Shiou-Hwa et al., "Overexpression of interleukin-6 in human basal cell carcinoma cell lines increases anti-apoptotic activity and tumorigenic potency", *Onogena 20* 2001, 198-208.

Jegasothy, Brian V. et al., "Tacrolimus (FK 506)—A New Therapeutic Agent for Severe Recalcitrant Psoriasis", *Arch Dermatol*, vol. 128 Jun. 1992, 781-785.

Johnson, JL et al., "Relationships between drug activity in NCI preclinical in vitro and in vivo models and early clinical trials", *British Journal of Cancer 94(10)* 2001, 1424-1431.

Jordan, V. C., "Tamoxifen: A Most Unlikely Pioneering Medicine", *Nature Reviews Drug Discovery*, vol. 2 2003, 205-213.

Karasek, Marvin A., "Progress in our understanding of the biology of psoriasis", *Cutis*, vol. 64, Iss. 5 Nov. 1999, 5 pgs.

Kaur, Charandeep et al., "An open trial of calcium dobesilate in patients with venous ulcers and stasis dermatitis", *International Journal of Dermatology 42* 2003, 147-152.

Khawli, Leslie A. et al., "Comparison of Recombinant Derivatives of Chimeric TNT-3 Antibody for the Radioimaging of Solid Tumors", *Hybridoma and Hybridomics*, vol. 22, No. 1 2003, 1-10.

Kocak, MD, Mukadder et al., "Examination of Bcl-2, Bcl-X and bax protein expression in psoriasis", *International Journal of Dermatology 42* 2003, 789-793.

Lameynardie, Stephane et al., "Inhibition of choroidal angiogenesis by calcium dobesilate in normal Wistar and disbetic GK rats", *European Journal of Pharmacology 510* 2005, 149-156.

Lens, M. et al., "Current clinical overview of cutaneous melanoma", *British Journal of Nursing*, vol. 17, No. 5 2008, 2 pgs.

Losa, Gabriele A. et al., "Preventionof Oxidation and Apoptosis in Human Peripheral Blood Mononuclear Cells Exposed to Caldium Dobesilate", *International Journal of Angiology 8* 1999, 511-515.

Lozano, Rosa M. et al., "Solution Structure of Acidic Fibroblast Growth Factor Bound to 1,3,6-Naphthalenetrisulfonate: A Minimal Model for the Anti-tumoral Actionof Suramins and Suradistas", *J. Mol. Biol. 281* 1998, 899-015.

Michal, M. et al., "Effect of Calcium Dobesilate on Platelet Function", *Thrombosis Research 51* 1988, 593-605.

Newell, B. et al., "Comparison of the microvasculature of basal cell carcinoma and actinic keratosis using intravital microscopy and immunohistochemistry", *British Journal of Dermatology 149* 2003, 105-110.

Niwa, Y. et al., "Topical applicationof the immunosuppressant tacrolimus accelerates carcinogenesis in mouse skin", *British Journal of Dermatology 149* 2003, 960-067.

Non-Final Office Action in U.S. Appl. No. 12/946,742, dated Dec. 30, 2011, 8 pgs.

Nour, A. F. et al., "Preliminary Clinical Study with Calcium Dobesilate in Fibrocystic Disease of the Breast", *Acta Therapeutica*, vol. 12. No. 3 1986, 233-241.

O'Grady, Anthony et al., "COX-2 Expression Correlates With Microvessel Density in Non-Melanoma Skin Cancer From Renal Transplant Recipients and Immunocompetent Individuals", *Human Pathology*, vol. 35, No. 12 2004, 1549-1555.

Oh, Chang-Keun et al., "Expression of Basic Fibroblast Growth Factor, Vascular Endothelial Growth Factor, and Thrombospondin-1 Related to Microvessel Density in Nonaggressive and Aggressive Basal Cell Carcinomas", *The Journal of Dermatology*, Vo. 30 2003, 306-313.

PCT IPRP in PCT/EP2007/058438, dated Nov. 21, 2008, 8 pgs.

PCT IPRP in PCT/EP2007/058439, dated Dec. 1, 2008, 6 pgs.

Pelle, Michelle T. et al., "Rosacea: II. Therapy", *J Am Acad Dematol*, vol. 51 2004, pp. 499-512.

Reply to Written Opinion in PCT/EP2007/058440, dated Jul. 17, 2008, 30 pgs.

Rhodes, Christopher T., "Modern Pharmaceutics, 3rd Edition, Revised and Expanded", *Marcel Dekker, Inc.*, 3 pgs.

Ruiz, Emilio et al., "Calcium Dobesilate Increases Endothelium-Dependent Relaxation in Endothelium-Injured Rabbit Aorta", *Pharmacological Research*, vol. 38, No. 5 1998, 361-366.

Rutkowski, Suzanne, "Mystified by Your Medications?", *Asthma Magazine* 2001, 9-12.

Sausville, Edward A. et al., "Contributions of Human Tumor Xenografts to Anticancer Drug Development", *Cancer Res 66*(7) Apr. 1, 2006, 3351-3354.

Schon, MD, Michael et al., "Psoriasis", *The New England Journal of Medicine* 2005, 1899-1912.

Schulze, H. J. et al., "Imiquimod 5% cream for the treatment of superficial basal cell carcinoma: results from a randomized vehicle-controlled phase III study in Europe", *British Journal of Dermatology 152* 2005, 939-947.

Sintov, Amnon C. et al., "Percutaneous penetration and skin metabolism of ethylsalicylate-containing agent, UT-2100: in-vitro and in-vivo evaluation in guinea pigs", *Journal of Controlled Release 79* 2002, 113-122.

Skov, L. et al., "Basal cell carcinoma is associated with high TNF-a release but not with TNF-a polymorphism at position 308", *Experimental Dermatology 12* 2003, 772-776.

Staibano, MD, S. et al., "The Prognostic Significance of Tumor Angiogenesis in Nonaggressive and Aggressive Basal Cell Carcinoma of the Human Skin", *Human Pathology*, vol. 27 No. 7 1996, 695-700.

Stanton, Anthony W. et al., "Expansion of Micorvascular Bed and Increased Solute Flux in Human Basal Cell Carcinoma in Vivo, Measured by Fluorescein Video Angiography", *Cancer Research 63* 2003, 3969-3979.

Stanwell, Caroline et al., "The Erbstatin Analogue Methyl 2,5-Dihydroxycinnamate Cross-Links Proteins and is Cytotoxic to Normal and Neoplastic Epithelial Cells by a Mechanism Independent of Tyrosine Kinase Inhibition", *Cancer Research*, vol. 55 1995, 4950-4956.

Stockfleth, E. et al., "Successful treatment of actinic keratosis with imiquimod cream 5%: a report of six cases", *British Journal of Dermatology*, 144 2001, 1050-1053.

Suschek, Christoph et al., "Dobesilate enhances endothelial nitric oxide synthase-activity in macro- and microvascular endothelial cells", British Journal of Pharmacology 122 1997, 1502-15-8.

Takatsuka, Yoshikazu et al., "Various Analogues to Anthranilic Acid and Their Anti-Cancer Effects", *Mie Medical Journal*, vol. XVII, No. 1 1987, 11 pgs.

Tejerina, T. et al., "Calcium Dobesilate: Pharmacology and Future Approaches", *Gen. Pharmac.*, vol. 31, No. 3 1998, 357-360.

Tjiu, Jeng-Wei et al., "Cyclooxygenase-2 Overexpression in Human Basal Cell Carcinoma Cell Line Increases Antiapoptosis, Angiogenesis, and Tumorigenesis", *The Society for Investigative Dermatology* 2006, 1143-1151.

Tjiu, Jeng-Wei et al., "Tumor-Associated macrophage-Induced Invasion and Angiogenesis of Human Basal Cell Carcinoma Cells by Cyclooxygenase-2 Induction", *Journal of Investigative Dermatology* 2009, 1016-1025.

Travis, Lisa et al., "Mdical Backgrounder: Psoriasis", *Drugs of Today*, 38 (12) 2002, 847-865.

Trozak, Daniel J., "Topical corticosteriod therapy in psoriasis vulgaris: Update and new strategies", *Cutis.*, vol. 64, Iss. 5 5 pgs., Nov. 1999.

Vippagunta, Sudha R. et al., "Crystalline solids", *Advanced Drug Delivery Reviews 48* 2001, 3-26.

Wilkin, Jonathan et al., "Standard classification of rosacea: Report of the National Rosacea Society Expert Committee on the Classification and Staging of Rosacea", *Acad. Derato. 46*:L 2002, 584-587.

Wolf, Manfred E. , "Burger's medicinal Chemistry and Drug Discovery", Fifth Edition vol. 1: *Principles and Practice* 1995, 4 pgs.

Wollina, U. et al., "Toxicity of Methotrexate Treatment in Psoriasis and Psoriatic Arthritis—Short and Long-Germ Toxicity in 104 Patients", *Clin Rheumatol 20* 2001, 406-410.

Written Opinion of PCT/EP2007/058438, mailed on Nov. 27, 2007, 7 pages.

Written Opinion of PCT/EP2007/058440, mailed on Feb. 22, 2008, 8 pages.

Written Opinion of PCT/ES2005/070017, mailed on Jun. 22, 2005, 3 pages.

Yamada, Katsuhisa et al., "Inhibitory Effect of Diacetyl Gentisic Acid on Melanogenesis", *Journal of Japanese Cosmetic Science Society*, vol. 22, No. 3 1998, 169-174.

Final Office Action in U.S. Appl. No. 12/946,742, mailed Jun. 15, 2012, 11 pgs.

Peck, M.D., Gary L., "Topical tretinoin in actinic Keratosis and basal cell carcinoma", *Journal of the American Academy of Dermatology*, vol. 15, Issue 4, Part 2—Abstract only—Oct. 1986, 2 pgs.

* cited by examiner

USE OF 2,5-DIHYDROXYBENZENESULFONIC ACID IN THE MANUFACTURING OF MEDICINES, APPLICABLE TO THE TREATMENT OF ANGIODEPENDENT DISEASES

SCOPE OF THE INVENTION

This invention refers to a pharmaceutical composition that includes the 2,5-dihydroxybenzenesulfonic acid, and its employment, in the preparation of a medicine for treatment of diseases characterized by an intense cell proliferation, vascularization (angiodependent diseases) and more specifically angiodependent diseases also having reduction of the apoptosis, as it is the case for example in cancer or psoriasis.

BACKGROUND OF THE INVENTION

Malignant tumors are characterized, besides from the uncontrolled cellular proliferation, by their capacity to invade normal peritumoral tissues. Tumor invasion is a complex process developed according to the following consecutive stages: a) adhesion of the tumor cells to proteins of the extracellular matrix; b) degradation of the proteins of the extra-cellular matrix by proteases that create extra-cellular spaces that the tumor cells use to, c) migrate through a dynamic and complex mechanism that requires synthesis of new portions of the cytoplasmic membrane and reorganization of the cytoskeleton (Giese A, Westphal M. Neurosurgery 1996; 39: 235-252). The cells that from the tumor mass invade the normal peritumoral-tissue have their genetic program of cellular death disabled and therefore, the tumor cells that migrate to invade the peritumoral intact tissues, elude the apoptosis (Mariani I et al. Clin Cancer Res 7:2480-2489, 2001). When the grouped tumor cells reach 2 to 3 $mm^3$ volume, the tumor cells synthesize large amounts of angiogenic factors to counteract the hypoxic situation of this primary tumor, (Folkman J. N. Engl J Med 285: 1182-1186, 1971; Carmeliet P, Jain R K. Nature 407; 249-257, 2000; Yancopoulos G D et al. Nature 407: 242-248, 2000) that activate the peritumoral blood vessels so that they form new blood vessels (angiogenesis) that invade the minor to supply the oxygen and the nutrients and eliminate products from the tumor catabolism. The same cellular processes that occur during the tumor invasion (motility and absence of apoptosis) occur centripetally during tumor angiogenesis. Therefore, the inhibition of the invasive capacity of the tumor cells and of the endothelial cells should produce a delay in tumor growth by inhibiting the tumor expansion, reducing angiogenesis and promoting apoptosis. Therefore, an effective treatment against cancer should inhibit the migration, the angiogenesis and increase apoptosis without producing these effects in normal cells.

There are numerous anti-tumor and antiangiogenic agents at various stages of clinical development in oncology (Brem S. Cancer Control 6: 436-458, 1999), of which a significant number are peptides that the body uses to counteract the effect of the positive regulators of angiogenesis (Hagerdorn M, Bikfalvi A. Crit Rev One Hemat 34: 89-110, 2000). However, when these peptides are compared with compounds with a significantly lower molecular weight, their pharmacological inconveniences become evident. On the other hand, it has been proven that different synthetic compounds containing aromatic rings in their molecular structure and acting as inhibitors of the mitogenic activity induced by growth factors are cytotoxic for quiescent or non tumor cells (Lozano R M J Mol Biol 281: 899-9115, 1998). Therefore, there is still need to find compounds with anti-tumor, antiangiogenic and proapoptotic activity with low toxicity for intact, quiescent, non tumor cells. There is presently a great interest for the search of new therapeutic indications for old medicines. In this connection, it has been recently proven that different antibiotics, besides from their antimicrobial activity, have antiproliferative effects, such in the case of rapamycin (Morice M C et al. N Engl J Med 346: 1773-1780, 2002), or of the neomycin (Cuevas P. et al. Neurol Res 224: 389-391, 2002); or are useful as anxiolytics such as norfloxacin (fluoroquinolone) (Johnstone T B et al, Nat Med 10; 31-32, 2004).

Psoriasis is an angiodependent chronic disease that affects 2-3% of the world population and is characterized by epidermic hyperplasia, dermo-epidermic infiltration of inflammatory cells and T lymphocytes, and a very evident development of vascularization, together with a reduction of the cell death due to apoptosis (Kocak M et al. Int J Dermatol 42: 789-793, 2003). Presently, there is no curative treatment for psoriasis. The antipsoriatic treatment may be topical or systemic, depending on the extension and severity of the disease. The mostly used anti psoriatic topical therapy consists of different types of corticoids, but the extended use of these compounds is associated with skin atrophy, stretch marks and telangiectasia (Baker B S, Fry L Cutis 1999; 64: 315-318). The systemic therapy with immunosuppressant medicines is associated to very severe side effects (Wolina V. et al. Clin Rheumatol 2001: 20: 406-410). For example, the use of cyclosporine for treatment of psoriasis may produce nephrotoxicity (interstitial fibrosis and tubular atrophy), hypertension, hypomagnesaemia, hypercalcemia and hepatic dysfunction (Travis L, Weinberg J M. Drugs of Today 2002; 38: 847-865). The standing use of another immunosuppressant medicine for treatment of psoriasis, tacrolimus, may produce hypertension, nephrotoxicity and immunosuppression (Jegasothy B V et at. Arch Dermatol 1992; 128: 781-785). It has been recently described that the topic application of the tacrolimus immunosuppressant accelerates carcinogenesis in mouse skin (Niwa Y, Terashima T, Sumi H. B J Dermatol 2003; 149: 960-967). Therefore, there is need for new antipsoriatic compounds proving to be efficient without producing evident side effects such is as those associated with the most common anti-psoriatic compounds.

The 2,5-dihydroxybenzenesulfonic acid is a derivative of the 2,5-dihydroxybenzoic acid, pharmacologically prescribed in the form of different salts (mainly calcium, potassium, and magnesium), which provides stability. The 2,5-dihydroxybenzenesulfonic acid has been used since the 70's as an oral vasculotropic medicine.

The 2,5-dihydroxybenzenesulfonic acid inhibits platelet aggregation, increase of capilar permeability and blood viscosity in patients with diabetic retinopathy (Bayer J. et al. Dtsch. Mod Wschr 1980; 46: 160-1608; Banarroch L S. et al Ophthalmic Res 1985; 17; 131-138; Michal M, Giessinger N. Thromb Res 1988; 51: 593-605). The metabolism and the pharmacokinetics of this compound in the human being is known since year 1974 (Benakis A. et al. Thérapie 1974; 29: 211-219). Recent experiments have proven that the 2,5-dihydroxybenzenesulfonic acid increases the activity of the endathelial isoform of the nitric oxide synthase [endothelial nitric oxyde synthase (eNOS)] in rat endothelia cis without producing cytotoxic effects (Suscheck C. et al. Bt J Pharmacol 1997; 122: 1502-1508). In addition, the 2,5-dihydroxybenzenesulfonic acid potentiates the in vitro relaxation of human penile arteries (Angulo J et al. Br J Pharmacol 2003; 139: 854-862). There is experimental evidence that the 2,5-dihydroxybenzenesulfonic acid (formulated as a calcium or magnesium salts) possesses in vitro antioxidant activities (Brunet J et al. Fundam Clin Pharmacol 12: 205-212, 1998).

SUMMARY OF THE INVENTION

The present invention is based on the discovery of new activities of the 2,5-dihydroxybenzenesulfonic acid and/or its salts, associated to their antiproliferative, anti migratory, antiangiogenic and proapoptotic capacity in non quiescent cells, activities that combined, justify their employment as a useful compound for treatment of angiodependent diseases such as the case of cancer, characterized by hyperproliferation, cell invasion and excessive angiogenesis, together with a deficit in cell death due to apoptosis, without causing toxicity for non-tumor intact or quiescent cells. Gliomic tumor cells have been used in experiments because gliomas are very invasive tumors with a significant angiogenic capacity and a significant apoptotic deficit (Merzak A, Pilkington G J. Cancer Metastasis Rev 16: 155-177, 1997).

The present invention is also based on the proven fact that the 2,5-dihydroxybenzenesulfonic acid and/or its salts possess, in a combined form, antiproliferative, antiangiogenic, and proapoptotic effects and therefore its therapeutic efficacy has been evaluated in chronic psoriatic plaques characterized by epidermic hyperproliferation, acute dermal angiogenesis and apoptotic deficit (Karasek M A, Cutis 64: 319-322, 1999).

This invention relates then to the search of new treatments for cancer and other angiodependent diseases an it is based on the fact that the 2,5-dihydroxybenzene sulfonic acid and/or its salts have proven their capacity to inhibit growth and migration and induce the apoptosis in in vitro tumor cells as well as the capacity to inhibit the in vivo angiogenesis induced by fibroblast growth factor (FGF). Therefore, due to the combination of these abilities, the mentioned compounds become useful for the treatment of malignant tumors and hematological neoplastic diseases as well as for treatment of other severe vascularization related pathologies (angiodependent diseases).

BRIEF DESCRIPTION OF THE DRAWINGS

FIG. 1A depicts 88% inhibition with a concentration of 100 μM of the calcium salt of the 2,5-dihydroxybenzenesulfonic acid. FIG. 1B depicts 74% inhibition with the same concentration of the potassium salt of the 2,5-dihydroxybenzenesulfonic acid;

FIG. 3A shows the results of treatment with the calcium salt of the 2,5dihydroxybenzenesulfonic acid. FIG. 3B show the results of treatment with the potassium salt of the 2,5dihydroxybenzenesulfonicacid;

DESCRIPTION OF THE INVENTION

The 2,5-dihydroxybenzenesulfonic acid formulated in the form of salt is a commercial product (for example, the potassium salt may be acquired at Merck Farma y Química SA, Mollet del Vallés, Barcelona) with the following molecular formula:

in which Met=Metal and n is a function of the metal valence used in the salt. Generally n 0 1 or 2 for being the metal cation former of the salt, univalent (K) or divalent (Ca δ Mg).

The new biological activities of the 2,5 dihydroxybenzenesulfonic acid do not depend of the cation bond to the benzene ring because the 2,5-dihydroxybenzenesulfonic acid formulated with any salt has similar effects in the inhibition of cell proliferation, migration and angiogenesis. This invention only describes the activities of the 2,5-dihydroxybenzenesulfonic acid formulated as potassium and calcium salt without forgetting that within the scope of this invention is any pharmaceutically acceptable salt of the compound. The term "pharmaceutically acceptable salts" include metal salts or addition salts which can be used in pharmaceutical forms. The pharmaceutically acceptable salts of the 2,5-dihydroxybenzenesulfonic acid can be obtained from organic or inorganic acids or bases, through conventional methods, by making the appropriate acid or base react with the compound.

The pharmaceutical compositions containing the 2,5-dihydroxybenzenesulfonic acid can be presented in any adequate administration form, for example, systemic, oral, parenteral, urethral, rectal or topical administration, for which the necessary pharmaceutically acceptable excipients will be included for formulation of the desired form of administration.

The following examples illustrate and support the invention and should not be considered as limitations of the scope of the invention.

EXAMPLE 1

Figure 1A:
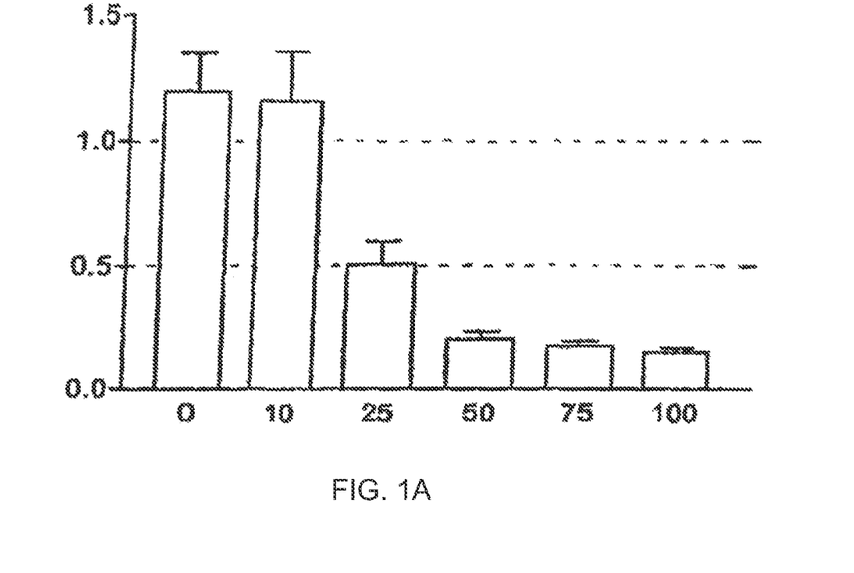
FIGS. 1A and 1B are graphs depicting treatment with different concentrations of a compound according to one embodiment producing a dose-dependent inhibition of cell proliferation.
Figure 1B:
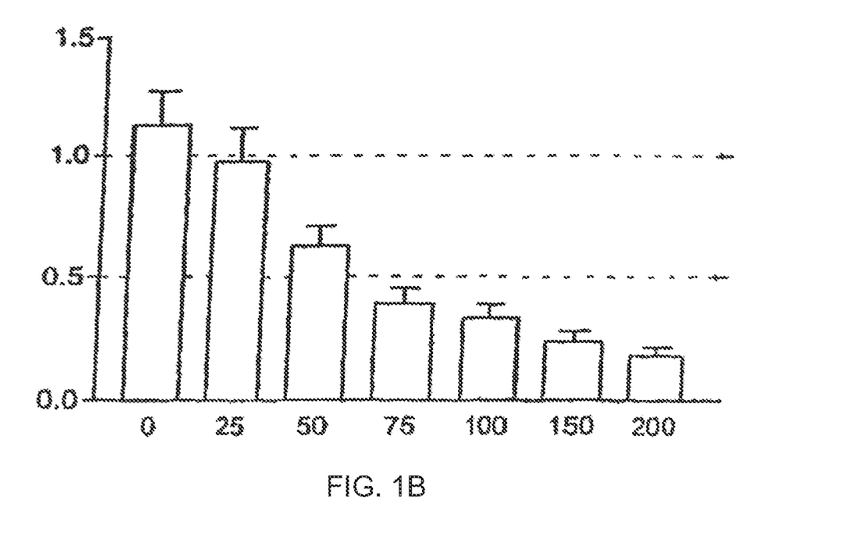
Figure 2A:
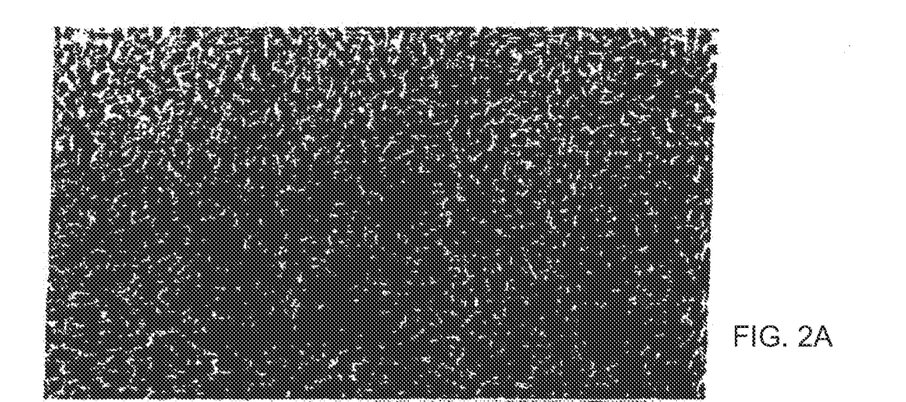
FIG. 2A shows the image of a C6 cell culture after 48 hours without treatment.
Figure 2B:
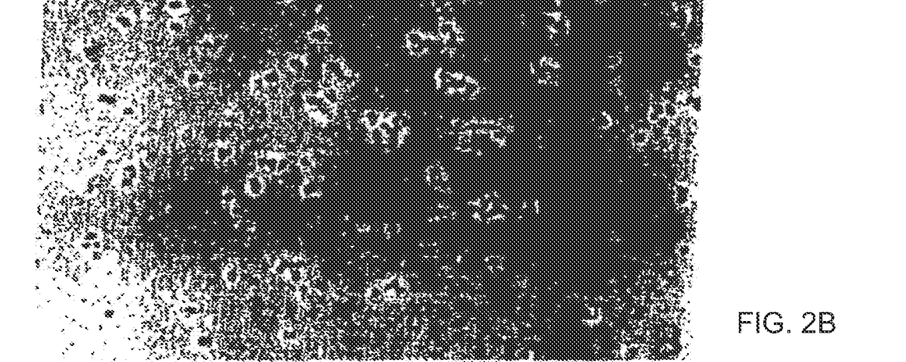
FIG. 2B shows the image of a C6 cell culture after 48 hours of treatment with a concentration of 50 μM of the calcium salt of the 2,5-dihydroxybenzenesulfonic acid.
Figure 2C:
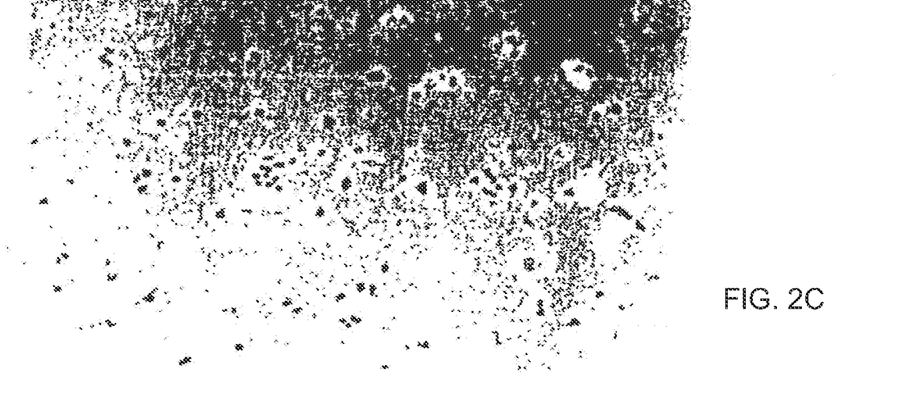
FIG. 2C shows the image of a C6 cell culture after 48 hours of treatment with 100 μM of the potassium salt of the acid.

Illustrative Assay of the Anti-proliferative Ability of the 2.5-Dihydroxybenzenesulfonic Acid This in vitro study, was carried out in three different triplicate experiments with rat gliomic is cells (C6 line). The cells were cultured in a medium formed by DMEM Dulbecco's modified Eagle's Medium (Gibco. Paisley UK), 7.5% of fetal serum (Gibco) 10 units/ml of penicillin (Gibco) and 10 μg/ml of streptomycin (Gibco). The cultures were kept in a humid atmosphere at 37° C. To evaluate the effect of the 2,5-dihydroxybenzenesulfonic acid on the cell proliferation, $2\times10^4$ C6 cells per well were seeded in 24-well (15 mm of diameter) plates. The experimental cultures were treated during 48 hours with different micro molar concentrations (μM) of the compound (calcium or potassium salt of the 2,5-dihydroxybenzenesulfonic acid). The controlled cultures lived 48 hours, without adding the compound. Photographs of the cultures were taken after 48 hours using an inverted microscope and then, the cultures were colored with crystal violet (Merck Farma y Química SA. Mollet del Vallés, Barcelona) and processed to determine the number of cells per well, using a spectrum photometric method. As shown in FIG. 1, treatment with different concentrations of the compound produces a dose-dependent inhibition of cell proliferation, obtaining 88% inhibition with a concentration of 100 μM of the calcium salt of the 2,5-dihydroxybenzenesulfonic acid (A). With the same concentration of the potassium salt of the 2,5-dihydroxybenzenesulfonic acid, a 74% inhibition was obtained (B). The $IC_{50}$ is near to 25 μM for the calcium salt and between 40 and 50 μM for the potassium salt. Comparing FIG. 1A with FIG. 1B, it is observed that to obtain the same percentage of inhibition in cell proliferation after treatment with the calcium salt of the compound, a double concentration of potassium salt is necessary to obtain the same effect. This is due to the fact that the calcium salt of the compound contains two active principle males (2,5-dihydroxybenzenesulfonic acid) that separate from salt in aqueous solution. FIG. 2 shows the image of the C6 cells culture after 48 hours without treatment (A), another image corresponding to the C6 cells culture treated for 48 hours with a concentration of 50 M of the calcium sat of the 2,5-dihydroxybenzenesulfonic acid (B) and a third one corresponding to a culture of C6 cells treated during 48 hours with 100 μM of the potassium salt of the acid (C). This study shows that the treatment with the compound inhibits proliferation in neoplastic cells and corroborates the antiproliferative effect of the is compound observed in normal vascular smooth muscular cells stimulated in vitro with mitogenic factors (Parés-Herbute N et al. Int J Angiol 8: S5-S10, 1999). To distinguish if the antiproliferative activity of the 2,5-dihydroxybenzenesulfonic acid is mediated by a cytotoxic or a proapoptotic effect, we conducted different experiments detailed in the following example:

EXAMPLE 2

Illustrative Assay of the Proapoptotic Ability of the 2,5-Dihydroxybenzenesulfonic Acid This assay was carried out with the C6 cells according to the procedure described in example 1. To demonstrate the proapoptotic effect of the analyzed compounds we have used two different methods that detect the intracellular fragmentation of the DNA and the apoptotic nuclei in situ.

Detection of the Intracellular Fragmentation of the DNA.

The enzymatic immunoassay methods to quantify the DNA fragments associated to histones may be considered suitable to determine the onset of apoptosis (Aragane Y et al. J Cell Biol 1998; 140: 171-182). This method allows to differentiate death due to necrosis from death due to apoptosis since in necrosis the cytoplasmic membrane is fragmented and the DNA appears in the culture medium, while in apoptosis, the fragmented DNA remains in the interior of the cell because the plasma membrane remains intact (Aragane Y et al. J Cell Biol 140: 171-182, 1998).

Using the Cell Death Detection ELISA$^{plus}$ kit (Boehringer Mannheim, Mannheim, Germany) in accordance with the manufacturer's instructions, we have determined the fragmentation of DNA in C6 ($2\times10^3$) cell cultures at 4, 16, 24 and 48 hours. The controlled cultures did not receive any treatment while from 50 to 200 μM (FIG. 3A) of the potassium salt of the 2,5-dihydroxybenzenesulfonic acid were added to the experimental cultures. Experiments were also conducted adding from 25 to 100 μM of the calcium salt of the 2,5-dihydroxybenzenesulfonic acid (FIG. 3B). All experiments were performed in triplicate in three different experiments.

Figure 3A:
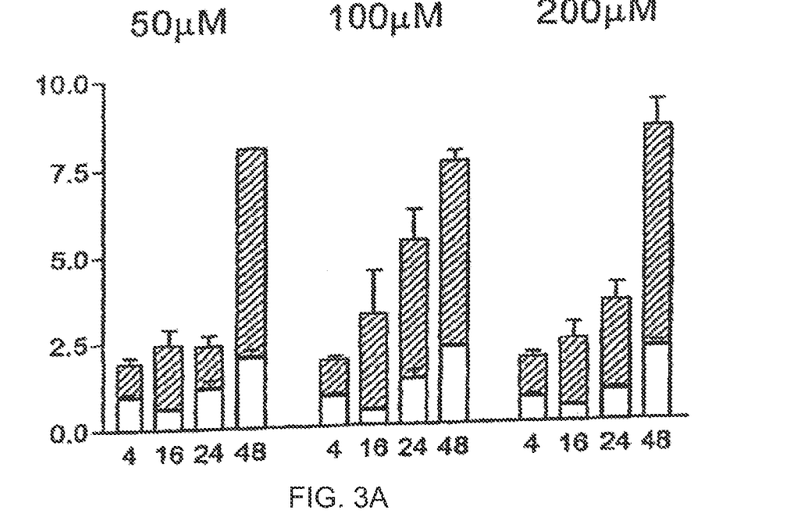
FIGS. 3A and 3B are representative graphs depicting the antiproliferative effect of the 2,5-dihydroxybenzenesulfonic acid.
Figure 3B:
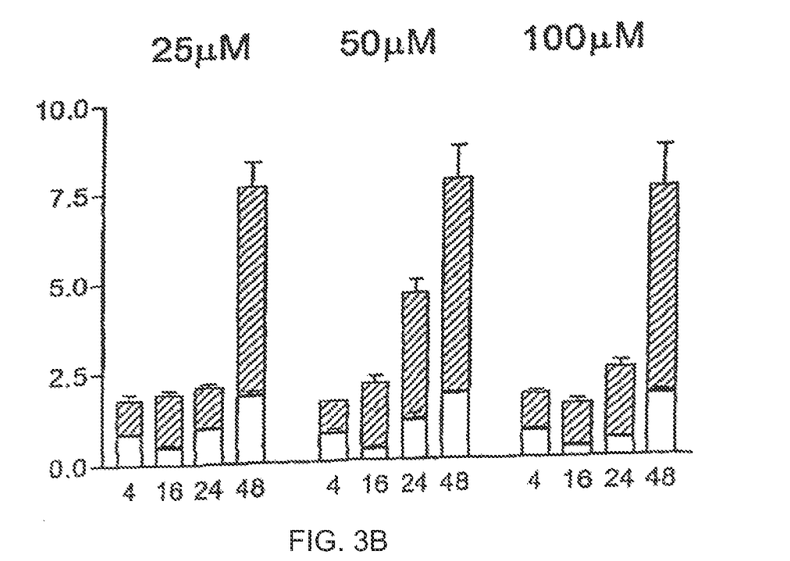
Figure 4A:
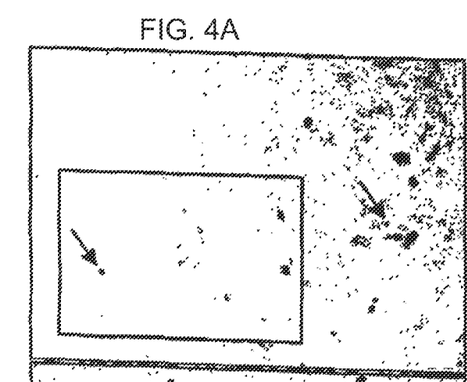
FIG. 4 shows the images of an area of an experiment of a control culture (FIGS. 4A and 4B) and of another culture treated with the compound (FIGS. 4C and 4D)
Figure 4B:
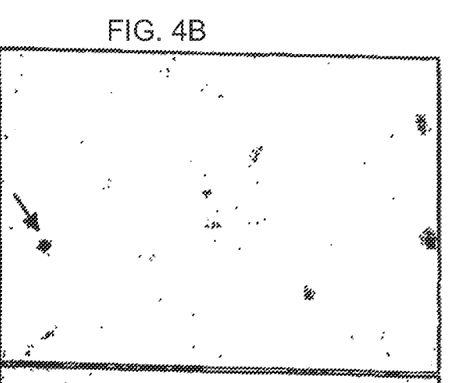
Figure 4C:
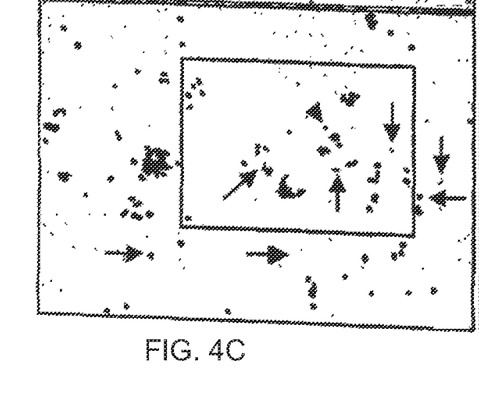
Figure 4D:
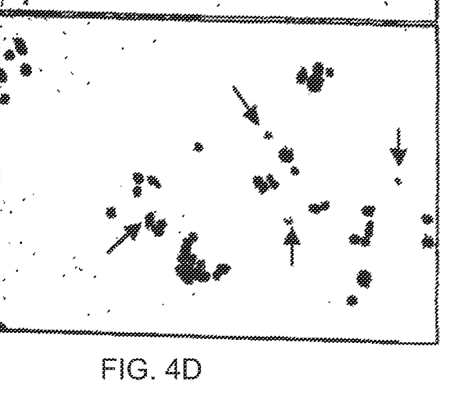
Figure 5A:
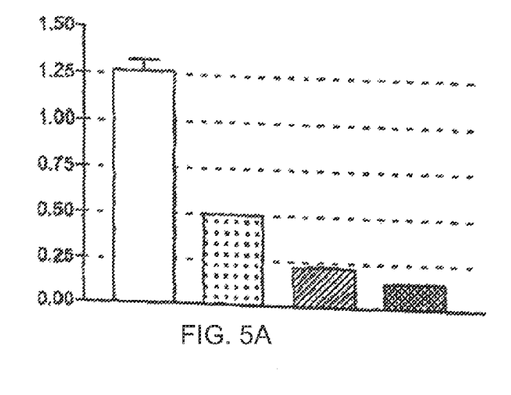
FIG. 5 shows histograms of the experiments to evaluate the effect of the 2,5-dihydroxybenzenesulfonic acid in the potentiation of the different cytostatic medicines: Cisplatin (5 μg/ml) (FIG. 5A); Vincristine (0.1 μl/ml) (FIG. 5B); Paclitaxel (5 μg/ml) ((FIG. 5C); and 5-fluorouracil (100 μg/ml) (FIG. 5D)
Figure 5B:
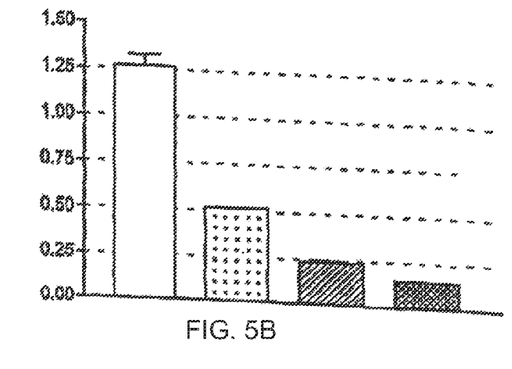
Figure 5C:
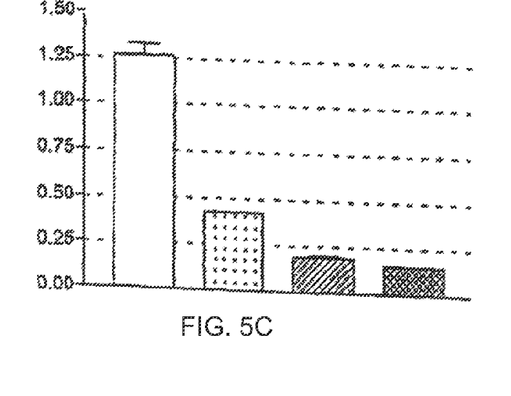
Figure 5D:
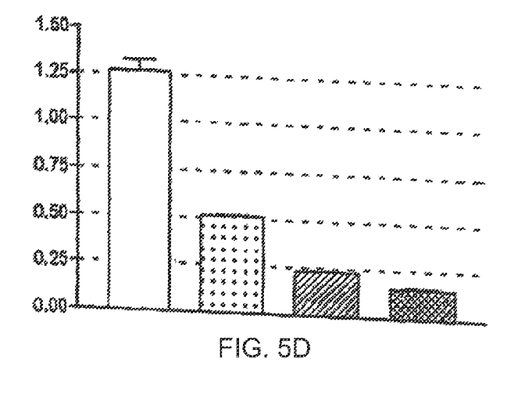

FIGS. 3A and 3B show the following: a) the antiproliferative effect of the 2,5-dihydroxybenzenesulfonic acid is mainly mediated by a proapoptotic activity; b) the cation bonded to the molecule does not determine the activity of the compound because the proapoptotic effect is similar using the calcium or potassium salt of the compound; c) the highest proapoptotic effect is obtained in cells treated with the compound during 48 hours; d) the maximum effect is obtained with a concentration of 25 μM for the calcium salt and 50 μM for the potassium salt, identical to the $IC_{50}$ in cellular proliferation studies. Once it is proven that the antiproliferative mechanism of the 2,5-dihydroxybenzenesulfonic acid participates in the cell death due to apoptosis, we quantitatively evaluated such effect through a microscopic study of gliomic cells using the following technique:

In situ Detection of a Apoptotic Nuclei (TUNEL Technique)

Three independent experiments were made, repeated three times. The C6 cells from controlled cultures and those from cultures treated during 24 hours with the (50 μM and 100 μM of the calcium and potassium salts respectively) were adhered to glass slides and fixed with a 4% paraformaldehyde buffered solution (pH 7.4) for one hour at the laboratory temperature. Afterwards, the cells were washed and permeabilized with a 0.1% solution of Triton X-100. Then the cells were washed before applying the TUNEL technique [(terminal deoxynucleotidyl transferase (TdT)-mediated dUTP nick and labeling (Gavrieli Y, Sherman Y, Bensasson S A. J Cell Biol 119: 493-501, 1992). A kit for in situ detection of apoptotic nuclei (In situ Cell Death Detection Kit Boehringer Mannheim, Mannheim, Germany) was used. The different stages of the technique were followed in accordance with the instructions of the kit manufacturer. Finally, the cells were colored with green light (Fluka, AG, Switzerland). The TUNEL reaction only appears in the apoptotic nuclei.

Although very similar results were obtained with the calcium and potassium salt of the compound, object of the invention, only the results obtained with the potassium salt of the compound are shown. Cells were counted in 6 different fields in twelve slides where the cells from the 6 control cultures and the 6 cultures treated with the 2,5-dihydroxybenzenesulfonic acid (100 μM) had adhered. The total number of non apoptotic and apoptotic cells was as follows:

| C6 Cells | Apoptotic Nuclei | Normal Nuclei |
|---|---|---|
| Control Cells | 138 | 5954 |
| Treated Cells | 3846 | 354 |

The total number of treated cells is lower than the total number of control cells due to the antiproliferative effect of the compound.

The images of FIG. 4 show an area of an experiment of a control culture (A and B) and of another culture treated with the compound (C and D) in which the TUNEL technique was employed. As shown in the images, only two apoptotic nuclei are observed on the control cells while in the treated cells with the compound object of the invention there are 107 apoptotic nuclei and only 8 normal nuclei (non apoptotic).

These data show that the 2,5-dihydroxybenzenesulfonic acid is a compound with an important proapoptotic activity useful to induce tumor apoptosis. Given that it has been proven that the 2,5-dihydroxybenzenesulfonic acid inhibits apoptosis in normal human cells (Braber R, Farine J C, Lora G A. Apoptosis 4; 4111-49, 1998), this compound is a strong molecule candidate for treatment of cancer.

One of the mechanisms involved in the therapeutic failure of chemotherapy and radiotherapy is the inefficacy of these treatments to induce cellular death by apoptosis, mainly due to the hyper expression of antiapoptotic proteins in tumor cells (Sellers W R, Fisher D E. J Clin Invest 104: 1655-1661, 1999; Branch P. et al. Oncogene 19: 3138-3145, 2000). Therefore, the proapoptotic compounds may be of great clinical use as an adjuvant in chemotherapy and radiotherapy treatments.

Once the proapoptotic effect of the 2,5-dihydroxybenzenesulfonic acid was demonstrated, we evaluated the ability of this compound to increase the antiproliferative effect of the different cytostatic medicines. The following example demonstrates how the 2,5-dihydroxybenzenesulfonic acid is capable of increasing the therapeutic efficacy of the different cytostatic compounds used in oncology such as cisplatin, vincristine, paclitaxel and 5-fluorouracil.

EXAMPLE 3

Illustrative Assay of the Ability of the 2,5-Dihydroxybenzenesulfonic Acid in Potentiation of Chemotherapy We used for this study C6 cells cultured in vitro under the same conditions described in example 1. $1\times10^3$ cells per well were cultured in 24-well plates. Three types of treatment were made: a) 24 hours after the seeding, the cells were separately treated with each one of the following medicines; cisplatin (5 µg/ml), vincristine (0.1 µg/ml), paclitaxel (5 µg/ml) and 5-fluorouracil (100 g/ml); b) 24 hours after the seeding, the cells were treated jointly with the 2,5-dihydroxybenzenesulfonic acid (potassium salt, 100 µM) and with each one of the following medicines; cisplatin (5 µg/ml) vincristine (0.1 µg/ml), paclitaxel (5 µg/ml) and 5-fluorouracil (100 µg/ml); c) at the time of the seeding (Day 0), the cells were pre-treated with the 2,5-dihydroxybenzenesulfonic acid (potassium salt, 100 µM). Next day the cultures were treated also with each one of the following medicines: cisplatin (5 µg/ml) vincristine (0.1 µg/ml), paclitaxel (5 µg/ml) and 5-fluorouracil (100 µg/ml). The controlled cultures did not receive treatment for 2 days. After 48 hours (day 2), the cells of identical shape to the ones used in example 1 were evaluated in all the cultures. This study was carried out in triplicate independent experiments repeated three times.

FIG. 5 (A, B, C and D) shows the histograms of the experiments performed to evaluate the effect of the 2,5-dihydroxybenzenesulfonic acid in the potentiation of the different cytostatic medicines. Treatment with cisplatin, vincristine and 5-fluorouracil produces an inhibition of 50% in proliferation of C6 cells, while the treatment with paclitaxel obtains 67% of inhibition of the cellular proliferation. The combined treatment of the 2,5-dihydroxybenzenesulfonic acid+the cytostatic medicines (cysplatin, vincristine and 5-fluorouracil) produces an inhibition of 84% in cellular proliferation. The combined treatment with 2,5-dihydroxybenzenesulfonic acid+paclitaxel produces 86% in the inhibition of the cellular proliferation. When cellular cultures are pre-treated with the 2,5-dihydroxybenzenesulfonic acid and afterwards with the following cytostatic medicines: cisplatin, vincristine and 5-fluorouracil, an inhibition of 90% is obtained in the cell proliferation. When paclitaxel is used, the inhibition in cellular proliferation reaches up to 92%.

The above mentioned results demonstrate that the simultaneous treatment of the 2,5-dihydroxybenzenesulfonic acid with the chemical therapy agents, increases their therapeutic efficacy and besides this chemical potentiation effect is higher when the cells has been pre-treated with the 2,5-dihydroxybenzenesulfonic acid. These data support the use of the 2,5-dihydroxybenzenesulfonic acid as an adjuvant in the treatment associated with chemical therapy and radiotherapy.

EXAMPLE 4

Figure 6A:
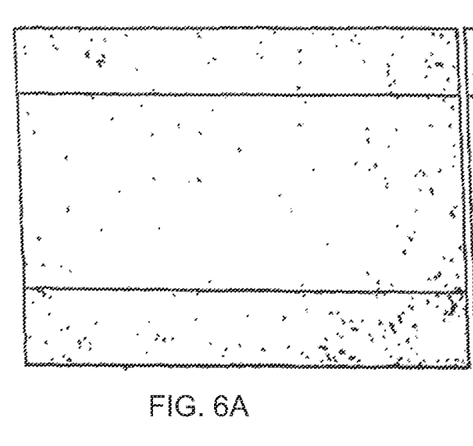
FIG. 6 shows images of a representative control experiment (FIG. 6A) and another experiment in which the cells were treated during 24 hours with the compound (FIG. 6B)
Figure 6B:
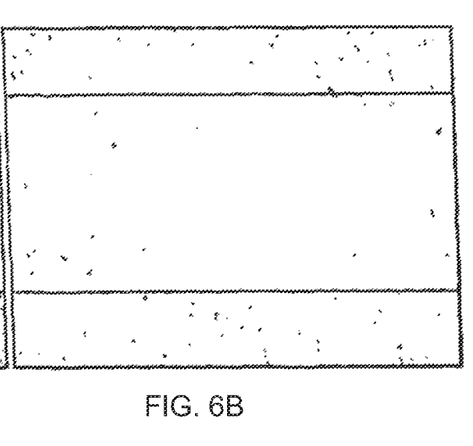
Figure 7:
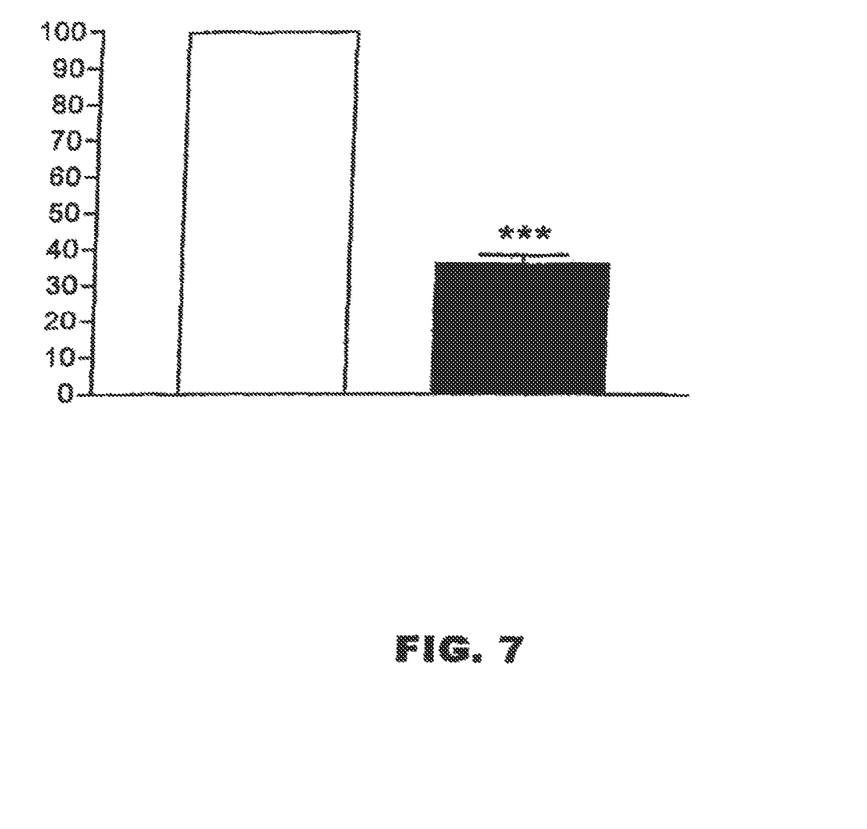
FIG. 7 is a graph representing the percentage data of all the experiments showing that the 2,5-dihydroxybenzenesulfonic acid inhibits up to 64% of migration of tumor cells.

Illustrative Assay of the Antimigration Ability of the 2,5-Dihydroxybenzenesulfonic Acid This assay was carried out in three different triplicate experiments. To evaluate the ability of the 2,5-dihydroxybenzenesulfonic acid in the inhibition of cellular migration C6 $2\times10^5$ cells cultured in vitro in 20 mm plates were used. A longitudinal lesion was made with a sterile micropipette (day 0) to the control cultures and in cultures treated with 100 µM of the potassium salt of the 2,5-dihydroxybenzenesulfonic acid. Digital photos were taken using a photographic system connected to a luminous microscope and the area of the lesion was delimited using a computerized morphometric program (Moticam Motic. Barcelona). Photographs were taken again after 24 hours, and the borders of the lesion were marked overlapping the first two photos (day 0) with those obtained after 24 hours to calculate the percentage of the injured area covered by the migratory cells. These values were represented as a percentage of the regeneration obtained with the treatment. FIG. 6 shows a typical example of a control experiment (A) and another experiment in which the cells were treated during 24 hours with the compound object of the invention (B). As observed in this Figure, the non treated cells completely regenerate the lesion (FIG. 6A) while the cells treated with the compound are not capable of migrating and cover all the area of the lesion (FIG. 6B). FIG. 7 that represents the percentage data of all the experiments shows that the 2,5-dihydroxybenzenesulfonic acid inhibits up to 64% of migration of tumor cells.

EXAMPLE 5

Illustrative Assay of the Antiangiogenic Ability of the 2,5-Dihydroxybenzenesulfonic Acid We used for this assay the chorioallantoic membrane of a chick embryo for testing the activity of antiangiogenic substances in vivo (Zilberberg L. et al. J Biol Chem 2003; 278:

35564-35573). We used a proangiogenic compound, the basic form of the fibroblast growth factor (bFGF) (Meghna U et al. Blood 2003; 102: 2108-2114).

Fertilized eggs are kept in a incubator at 37° C. with a humidity of 80%. After 4 days, a hole is made in the narrowest end of the egg shell to collect 1 ml of albumin Then, the hole is covered with a paraffin film (Parafilm M Laboratory Film Chicago Ill. USA). This procedure allows creating an air chamber that prevents the embryo to adhere to the upper part of the shell. On day 13 of incubation, the shell is split at the air chamber level to perform the treatment. Twenty embryos are treated with 5 µl of a solution of 3 µg of bFGF+0.1% heparin, soaked in a nitrocellulose paper disc. Afterwards the shell is sealed with a paraffin film. Next day, in half of the embryos (n=10) the shell is uncovered to soak again the nitrocellulose paper disc with 100 µM of potassium salt of the 2,5-dihydroxybenzenesulfonic acid dissolved in physiological saline (5 µl). The hole in the shell is then covered again with a paraffin film. On day seventeen the experiment ends, taking photographs of the nitrocellulose piece for the comparison study.

Figure 8A:
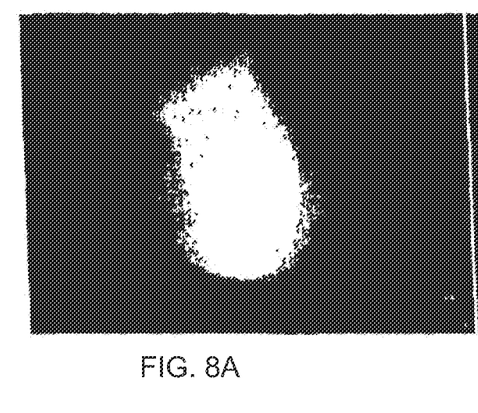
FIGS. 8A and 8B show the images corresponding to an embryo treated with 3 μg of bFGF+0.1% heparin (FIG. 8A) and another embryo to which 100 μM of a potassium salt solution of the 2,5-dihydroxybenzenesulfonic acid was added on the next day (FIG. 8B)
Figure 8B:
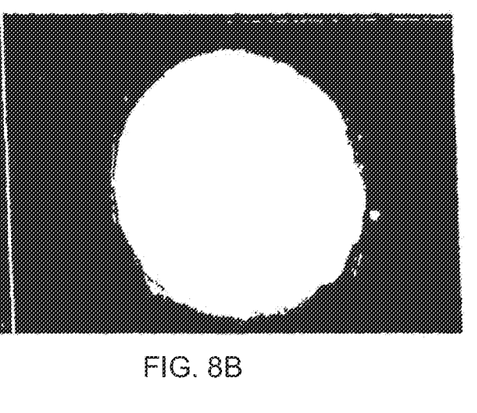

FIG. 8 presents two images corresponding to an embryo treated with 3 µg of bFGF+0.1% heparin (A) and another embryo to which 100 M of a potassium salt solution of the 2,5-dihydroxybenzenesulfonic acid was added on the next day (B) Image A shows how the nitrocellulose disc is invaded by blood vessels while Image B shows a very scarce vascular invasion in the disc. The morphometric quantification of the images of the nitrocellulose discs using a computerized system (Moticam Motic. Barcelona) shows the antiangiogenic effect of the compound (area of the disc covered by blood vessels in embryos treated with bFGF+heparin=35±8.6% vs. area of the disc covered by blood vessels in embryos treated with bFGF+heparin+potassium salt of the 2,5-dihydroxybenzene sulfonic acid=2±1.5%; $p<0.0001$; unpaired student's t-test). Similar effects were obtained using 50 µM of the calcium salt of the compound. This experiment shows that the compound object of this invention has an antiangiogenic activity for being capable of neutralizing the angiogenic effect induced by bFGF.

EXAMPLE 6

Assay on Psoriatic Lesions

We used for this study the potassium salt of the 2,5-dihydroxybenzenesulfonic acid formulated at 2.5 and 5% in cream for being this type of formulation a usual procedure for topical treatment of skin diseases. The selected concentrations of the salts of the 2,5-dihydroxybenzenesulfonic acid are within the range of the concentrations used for treatment of diabetic retinopathies: 6 tablets per day of 500 mg of calcium salt of the 2,5-dihydroxybenzenesulfonic acid (Benakis A et al Thérapie 1974; 29: 211-219). As aqueous phase of the cream we have used distilled water. The fatty phase can be constituted by cetylic alcohol, stearic alcohol or vaseline. The span is an efficient emulsifier in the preparation of the cream. Although both formulations (2.5 and 5%) of the product show to be clinically efficient, the best therapeutic benefit is obtained with the concentration at 5%. Therefore, we present the results obtained with the acid formulated in the cream at 5%. The following example illustrates the formulation of an efficient cream for the topic treatment of psoriasis, by way of example and not of limitation of the scope of the invention.

I.—Active Part (potassium salt of the 2,5-dihydroxybenzenesulfonic acid at 5.6%)
II.—Inactive Part (as excipients cetylic alcohol (2.5%), stearyl alcohol (2.5%), liquid vaseline (30%), white soft paraffin (20%), sorbitan oleate (5%) and distilled water (c.s.p. 100 g).

Figure 9:
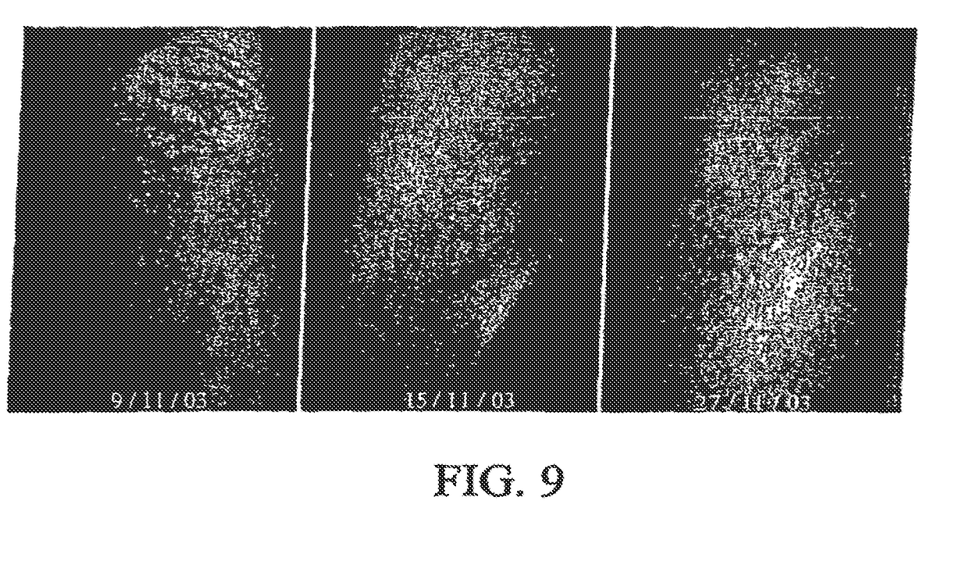
FIG. 9 shows images before treatment, at six and at thirteen days after treatment of the same chronic psoriatic plaque located in the extension area of the left elbow treated with the potassium salt of the 2,5-dihydroxybenzenesulfonic acid at 5%.

The clinical efficacy of the treatment was evaluated according to the index that quantifies the desquamation signs (D), erythema (E) and infiltration (I) to which the following assessment was assigned: (0) absent; (1) slight; (2) moderate and (3) severe (Freeman A K et al. J Am. Acad Dermat 2003; 48: 564-568). FIG. 9 shows three images: before treatment, six and thirteen days after treatment of the same chronic psoriatic plaque located in the extension area of the left elbow treated with the potassium salt of the 2,5-dihydroxybenzenesulfonic acid at 5%. As can be observed, the topical treatment two times at day with a cream containing the potassium salt of the 2,5-dihydroxybenzene sulfonic is acid produces an early (6 days) very notable "clearance" of the plaque with almost total disappearance of hyperkeratosis. The therapeutic efficacy of the cream is more evident at the end of the second, week of treatment. The treatment produces a significant reduction of the global values of the DEI index (DEI global pre-treatment=6±1.57 vs. DEI global post-treatment 1±0.58; $p<0.0001$; unpaired student's t-test).

Figures Captions

1. Histogram showing the antiproliferative effect of the treatment with different concentrations of the (A) calcium and (B) potassium salts of the 2,5-dihydroxybenzenesulfonic acid in cultures of C6 cells after 48 hours of treatment. Ordinates: Absorbance at 595 nm; Abscises: concentration: µM.
2. Panel A shows the aspect of a control culture of C6 cells after 48 hours. Panel B shows an image of a culture of C6 cells treated during 48 hours with 50 µM of the 2,5-dihydroxybenzenesulfonic acid (calcium salt). Panel C shows a culture of C6 treated during 48 hours with 100 µM of the potassium salt of the 2,5-dihydroxybenzenesulfonic acid.
3. Representative histograms in which it is observed that the antiproliferative effect of the 2,5-dihydroxybenzenesulfonic acid is not due to necrosis (white histogram) but to apoptosis (lined histogram). A: treatment with the calcium salt of the 2,5-dihydroxybenzenesulfonic acid. B: Treatment with the potassium salt of the 2,5-dihydroxybenzenesulfonic acid. Ordinates: Absorbance at 405 nm; Abscises: time in hours.
4. Images of gliomic C6 cells processed with the TUNEL technique for in-situ detection of apoptotic cells. The apoptotic nuclei are shown dark and the nucleus and cytoplasm of the cell of the non apoptotic cells are shown in light color. The arrows indicate apoptotic nucleus. A and B control cells, C and D cells treated with 2,5-dihydroxybenzenesulfonic acid. Photographs B and D correspond to a zoom of the boxes of A and C photographs respectively.
5. Histograms demonstrating the potentiating effect on chemotherapy (assessed as an antiproliferative effect) of the 2,5-dihydroxybenzenesulfonic acid, with different cytostatic compounds A) Cisplatin (5 µg/ml); B) Vincristine (0.1 µl/ml); C) Paclitaxel (5 Ug/ml) and D) 5-fluorouracil (100 µg/ml). Ordinates: Absorbance 595 nm; Abscises: white histogram (control); dotted (cytostatic; day 1); lined histogram (2,5-dihydroxybenzenesulfonic acid+cytostatic; day 1); square histogram (2,5-dihydroxybenzenesulfonic acid (day 0) 4 cytostatic; day 1).

6. Photographic images of cellular migration in a control experiment and other experiments where the cells were treated with the 2,5-dihydroxybenzenesulfonic acid (B). The control cells totally regenerate one lesion made during the culture, while the cellular migration of the cells treated with the 2,5-dihydroxybenzenesulfonic acid, was unable to fully cover the affected area of the culture. The horizontal lines delimit the initial longitudinal lesion made in the cultures.

7. Histogram representing the migratory ability of the C6 cells in controlled cultures (white histogram) and in cultures treated with the 2,5-dihydroxybenzenesulfonic acid (black histogram). The migratory ability is expressed (ordinates) as a percentage of regeneration (percentage of the area covered of a longitudinal lesion made in the cultures)

8. Images of two chicken embryos with 17 days of incubation. Panel A corresponds to an embryo treated with 3 µg of bFGF+0.1% of heparin. Panel B shows the aspect of an embryo treated with 3 µg of bFGF+0.1% de heparin+ 100 µM of the potassium salt of the 2,5-dihydroxybenzenesulfonic acid. Panel A shows the antiangiogenic effect of the 2,5-dihydroxybenzenesulfonic acid because the nitrocellulose disc used as releasing vehicle of the substance appears almost without any vessels.

9. Images of a hiperkeratosic psoriatic plaque located in the rear region of the left elbow. Image A represents the aspect of the psoriatic plaque before initiating treatment. Image B is an aspect of the same plaque after six days of treatment with a cream at 5% containing as an active component the potassium salt of the 2,5-dihydroxybenzenesulfonic acid. Image C shows the aspect of the psoriatic plaque after two weeks of treatment with the potassium salt of the 2,5-dihydroxybenzenesulfonic acid formulated at 5%. The numbers shown in the images correspond to the day on which the photographs were taken.

The invention claimed is:

1. A method of treating plaque psoriasis, comprising topically administering an effective amount of 2,5-dihydroxybenzenesulfonic acid or any of its pharmaceutically acceptable salts to an individual in need thereof.

2. The method of claim 1, wherein the pharmaceutically acceptable salt is the potassium salt of the 2,5-dihydroxybenzene sulfonic acid.

3. The method of claim 1, wherein the pharmaceutically acceptable salt is the calcium salt of the 2,5-dihydroxybenzene sulfonic acid.

4. The method of claim 1, wherein the 2,5-dihydroxybenzenesulfonic acid compound is formulated with at least one pharmaceutically acceptable excipient.

5. The method of claim 4, wherein the 2,5-dihydroxybenzenesulfonic acid compound is administered in the form of a cream.

6. The method of claim 1, wherein the individual in need thereof is a human.

7. The method of claim 1, wherein the 2,5-dihydroxybenzenesulfonic acid compound is administered twice daily.

8. The method of claim 1, wherein 2,5-dihydroxybenzenesulfonic acid compound is administered for at least 6 days.

9. The method of claim 8, wherein 2,5-dihydroxybenzenesulfonic acid compound is administered for 14 days.

10. The method of claim 1, wherein the treatment results in clearance of plaque.

11. The method of claim 1, wherein the treatment results in disappearance of hyperkeratosis.

12. The method of claim 1, comprising topically administering to a human patient in need thereof twice daily a cream comprising the potassium salt of the 2,5-dihydroxybenzene sulfonic acid at a concentration of 5.6% for at least 6 days, wherein the treatment results in clearance of plaque and disappearance of hyperkeratosis.

13. A method of treating plaque psoriasis, consisting of topically administering 2,5-dihydroxybenzenesulfonic acid or of any of its pharmaceutically acceptable salts to an individual in need thereof.

14. The method of claim 13, wherein the pharmaceutically acceptable salt is the potassium salt of the 2,5-dihydroxybenzene sulfonic acid.

15. A method of treating psoriasis consisting of topically administering 2,5-dihydroxybenzenesulfonic acid or of any of its pharmaceutically acceptable salts to an individual in need thereof.

16. The method of claim 15, wherein the pharmaceutically acceptable salt is the potassium salt of the 2,5-dihydroxybenzene sulfonic acid.

* * * * *